US006784826B2

(12) United States Patent
Kane et al.

(10) Patent No.: US 6,784,826 B2
(45) Date of Patent: Aug. 31, 2004

(54) BODY MOTION TRACKING SYSTEM

(75) Inventors: Ronald J. Kane, Pleasanton, CA (US); David Stevenson Spain, Jr., Portola Valley, CA (US)

(73) Assignee: Tera Research Incorporated, Sunnyvale, CA (US)

( * ) Notice: Subject to any disclaimer, the term of this patent is extended or adjusted under 35 U.S.C. 154(b) by 194 days.

(21) Appl. No.: 09/770,237

(22) Filed: Jan. 26, 2001

(65) Prior Publication Data

US 2002/0145563 A1 Oct. 10, 2002

(51) Int. Cl.$^7$ .............................................. G01S 13/00
(52) U.S. Cl. ........................ 342/28; 342/27; 342/118; 342/127; 342/147; 342/156; 342/195; 342/424; 342/442
(58) Field of Search ................................ 342/118, 127, 342/417–449, 27, 28, 42, 43–51, 56, 142, 151, 175, 195, 450–465; 340/540, 541, 552–567, 573.1, 574, 575, 576, 573.2, 573.3, 573.4, 573.7

(56) References Cited

U.S. PATENT DOCUMENTS

| | | | | |
|---|---|---|---|---|
| 3,286,263 A | * | 11/1966 | Hammack | 342/463 |
| 3,706,096 A | * | 12/1972 | Hammack | 342/461 |
| 3,795,911 A | * | 3/1974 | Hammack | 342/463 |
| 3,996,590 A | * | 12/1976 | Hammack | 342/465 |
| 5,596,330 A | * | 1/1997 | Yokev et al. | 342/465 |
| 5,719,584 A | * | 2/1998 | Otto | 342/465 |
| 5,790,076 A | * | 8/1998 | Sypniewski | 342/465 |
| 5,883,598 A | * | 3/1999 | Parl et al. | 342/457 |
| 5,999,131 A | * | 12/1999 | Sullivan | 342/465 |

OTHER PUBLICATIONS www.Trakus.com, Trakus, Inc., Medford, Ma; accessed on May 13, 2000.

* cited by examiner

Primary Examiner—Bernarr E. Gregory
(74) Attorney, Agent, or Firm—Thomas N. Giaccherini

(57) ABSTRACT

Methods and apparatus are disclosed for measuring position and motion of a "marker" antenna (14), disposed on a subject (12) at a physical location to be tracked. Relative distance of the marker antenna (14) from receiving antennas (18) is measured by phase differences of its microwave signals (40) at the receiving antennas (18) for at least two successive marker positions. Alternatively, actual distances (104, 106) are calculated by choosing a source position (102) and iterating the distances (104, 106) until the calculated phase differences match those measured. Four to six receiving antennas (18) are positioned at edges of a volume (16) where activity is conducted. Each received signal (40) is amplified and down-converted in a mixer (44). A single reference oscillator (46) feeds all the mixers (42) to preserve phase relationships of the received signals. Received signals (40) are digitized and presented to a multi-channel digital tuner (50). Phase relationships are preserved because all of the signal processing up to this step is "coherent". The digital data is fed (51) to a main computer and processed by algorithm to estimate the marker antenna's position relative to each receiving antenna (18). The apparatus is especially applicable to clinical gait analysis, sports medicine, industrial, military and entertainment uses.

27 Claims, 8 Drawing Sheets

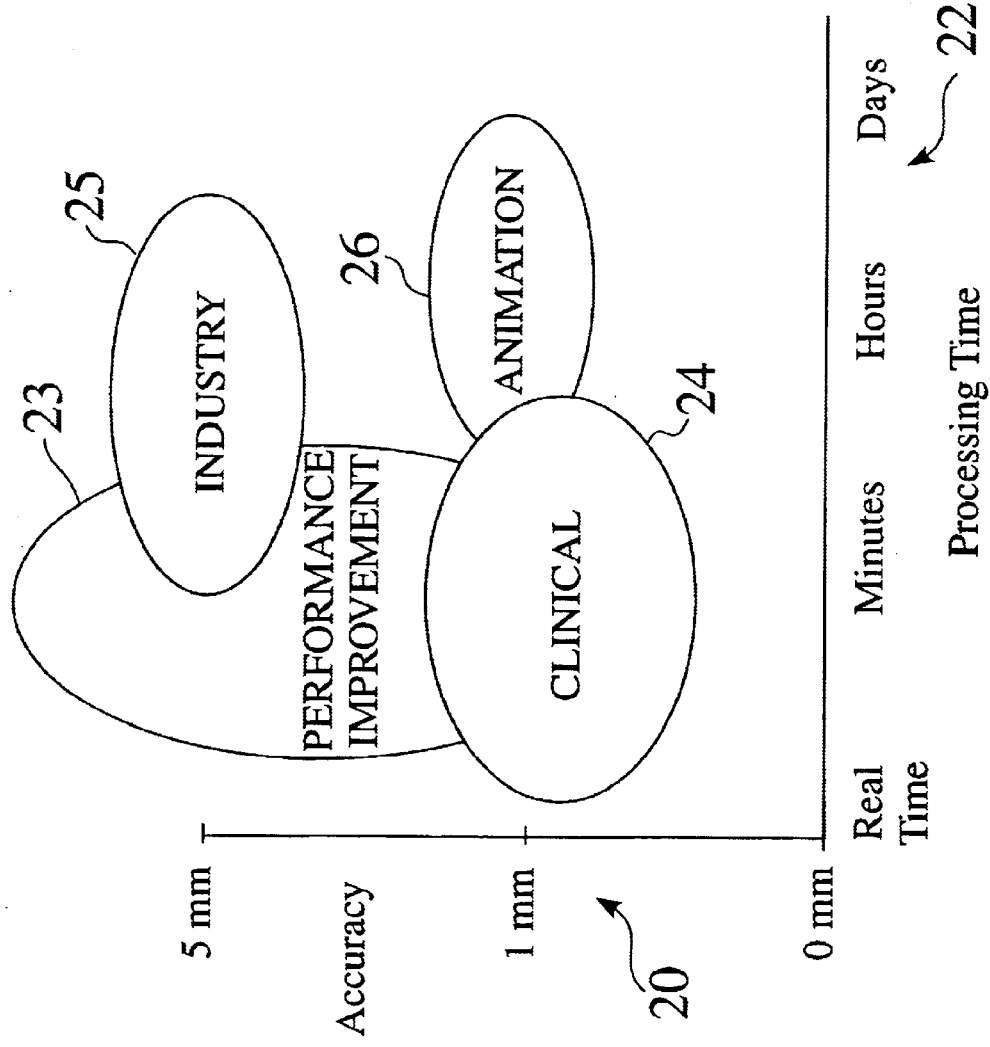

BODY MOTION TRACKING SYSTEM

FEDERALLY SPONSORED RESEARCH OR DEVELOPMENT

None.

FIELD OF THE INVENTION

The present invention relates to the field of motion analysis. More particularly, the invention pertains to clinical research and health care for persons with disabilities, athletes and athletic coaches, and the sports and entertainment industries.

BACKGROUND OF THE INVENTION

Motion study has been of interest for a great many years, particularly that relating to the human body. Sequential pictures of body movement was a subject of early photography. In the early 1970's a system for quantizing human locomotion, was developed, and methods of joint motion measurement since then. Several types of measuring techniques are now being used: electromechanical linkage; stereometric; accelerometeric; magnetic coupling; biplanar roentgenographic; and radio frequency (RF). Most of these methods are expensive to install and maintain, may be sensitive to interference by body parts, take time to get results and present difficulties in reducing and interpreting the data. The Roentgenographic method, though accurate, presents the hazard of ionizing radiation which is harmful to living subjects.

RF methods have been seriously investigated as an alternative since about 1994. These methods are relatively inexpensive, offer real-time motion capture capability, have high sampling rates, very good resolution and accuracy. The Lawrence-Livermore National Laboratory (Laboratory) and San Diego Children's Hospital and Health Center (CHHC) together developed RF concepts in 1994. At the same time, Softimage of Montreal, Canada was interested in respect of video games.

Over twelve million people in the United States have lower extremity disabilities, according to the U.S. Dept. of Health and Human Services (1994). Five-hundred thousand Americans have cerebral palsy, growing at the rate of 4,500 cases per year. Clinical gait analysis is a diagnostic tool for prescribing treatment for patients who suffer with neuromuscular, musculoskeletal, or neurological impairments. The primary goal in treating a person who has these problems is to correct their functional deficiencies and thereby improve their quality of life. Functional deficiencies are quantified analytically by having the subject perform simple tasks while patterns of limb movements are systematically measured. Motion-capture data reduces the number of surgeries required to correct some problems.

Trakus, Inc. of Medford, Mass., in their Internet site http://www.Trakus.com, describe an RF system which converts object motion into digital data that can be analyzed or used for entertainment purposes. Their product, designed for hockey and football, provides information about an athlete's movements on the playing field. Each athlete wears a transmitter which weighs two ounces. The transmitters send signals to antennas that surround the playing field. The system operates in spread spectrum because of the presence of other RF signals at base frequency of 2.45 GHz. The system uses time of arrival (TOA) measurements to calculate a player's position on the field. Sample rate of these measurements is about 30 times per second for each player on the field.

Providing a method and apparatus for real-time measurement of human body motion has been a continuing problem for clinical researchers, athletic coaches and live-sports commentators, to name a few. There is a great emphasis on knowing the outcome of medical treatment and extraordinary interest in using such motion information to enhance competitive athletics and to complement sports, industry, the military and entertainment. The inability of currently-used technology, to provide inexpensive, real-time analysis of the motion of limbs and joints has been frustrating. This is particularly true of widely used optical systems. Relatively new radio frequency approaches have not yet been applied to the detailed measurements required for the applications mentioned above. Producing analytical measurement of human motion, at a high sampling rate and with high resolution will revolutionize the field of human performance analysis, among other things, by expanding the range of application and reducing the cost of necessary healthcare for disabled persons. Solving these problems would constitute a major technological advance and would satisfy a long felt need in medicine, athletics, and recreation and entertainment industries.

SUMMARY OF THE INVENTION

An objective of the present invention is to develop a precision position measurement system that uses radio frequency (RF) phase interferometry. Energy sources, which are transmitting antennas disposed on a subject, are continuously located by receiving apparatus to a resolution of one millimeter (mm). This data is used, for example, in clinical gait analysis applications. Advantages include significant time savings for data analysis, real-time motion acquisition and display, high frame-rate acquisition, full body motion acquisition and reduced data loss from occlusion of markers on the subject. Enhancement of human body motion performance is an end result. Two methods of measuring position are contemplated.

The first measurement method uses a single antenna at each of several widely separated receiving locations to "triangulate" each energy source. By examining the differences in signal phase at pairs of receiving locations, source position is determined by one of two approaches. A first approach uses a known starting position for a source and computes changes in position. A second approach computes position by examining the enclosed volume for physical positions where the measured phase relationship would occur.

The second measurement method uses a small array of antennas at each of several receiving locations. Each array is able to determine the direction of arrival of the transmitted signal and the transmitter location is determined from the intersection of the direction-of-arrival vectors.

While the discussion which follows focuses on human body motion as an example, the measurement techniques of this invention can also be applied to animals, robotics, mechanical metrology and other articulated bodies and machines.

The Body Motion Tracking System measures path lengths to a number of receiving antennas from a source or "marker" antenna, disposed on a subject at a physical location to be tracked, to provide an estimate of the source's position time history.

Four to six receiving antennas are positioned at the edges of a volume in which activity is being conducted. Each antenna is coupled to a preamplifier which drives a mixer. In a preferred embodiment, the received signal is down-converted to translate the RF energy from microwave frequency to an intermediate frequency (IF) of about three Megahertz (MHz). A single reference oscillator must be fed to all of the mixers in order to preserve the phase relationships of the RF signals from the receiving antennas. The IF signals are presented to a bank of analog-to-digital converters which transform the analog signals to a digital signal format. A common sampling clock, operating in one embodiment at sixteen MHz, is used in this conversion process. Choice of clock frequency depends on the hardware selected and whether direct or sub-sampling is desired. The use of a common clock is required to preserve the phase relationships of the RF signals received.

Digital representations of the received signals are presented to the inputs of a multi-channel digital tuner. The digital signals are translated again to about one KHz. Narrow-band filtering and sampling rate reduction are applied. Phase relationships are still preserved because all of the signal processing up to this step is "coherent."

The digital data is fed to a main computer and processed to estimate each marker antenna's position. There are significant differences between this technique and conventional direction finding techniques.

Conventional DF systems consist of a number of small arrays of receiving antennas. They operate with the assumption that the range from a source to a receiving antenna is very large relative to the spacing of the antennas in the receiving array. As a result, the RF energy wavefront can be represented as a "plane wave" at the receiving array. In conventional DF systems, each receiving location measures the "angle of arrival" of the RF energy with respect to a system reference direction by phase measurement at adjacent pairs of antennas. The position of the source is estimated by "triangulation," that is, finding the intersection of lines drawn from each of three or more receiving locations, along the angle of arrival measured at that location.

The present invention employs differential phase measurement between pairs of widely spaced antennas to determine source position. The range (distance) from a transmitter (source) to a receiver uniquely determines the phase difference between the transmitted and the received signals. The difference in the ranges from a transmitter to two receivers uniquely determines the phase difference in the two received signals. The locus of points with the same range difference is one-half of a hyperbola of revolution with the two receivers as foci. Thus, barring abnormal placement of the receive antennas, the range difference for three pairs of antennas (four antennas total) determines a unique transmitter position within a workspace.

In one preferred embodiment of the present invention, the source transmits a continuous wave (CW) signal, i.e., a sine-wave. All range differences that differ by an integer number of wavelengths for a pair of receiving antennas, produce the same value of phase difference. Therefore, the locus of points having the same phase difference at a pair of receiving antennas is a family of hyperbolas of revolution having the two antennas as foci. Adjacent hyperbolas are one-half wavelength apart where they intersect the line joining the two antennas. Phase difference measurements using several pairs of receiving antennas may produce many equally valid solutions for transmitter position. However, if the volume of space containing the correct solution is suitably constrained, the phase difference measurements will produce only one valid solution.

Changes in the transmitter position will alter the lengths of the signal paths and therefore the phases of the received signals. However, if an estimate of the position of a transmitter is available and the next set of phase difference measurements is made when the transmitter could not have moved more than a small fraction of wavelength, then the volume in which the new transmitter position must be found is small enough to contain only one solution to the phase-difference equations and the new position can be determined uniquely. Because of the physics of RF propagation in a linear, isotropic medium, changes in phase difference measurements from time-to-time are due to transmitter movement.

The present invention contemplates several methods of establishing an initial position of the transmitter antenna. Each method may be appropriate for different applications of the invention. The simplest method requires the transmitter antenna to start from a particular position. A second method, using a small array of antennas at each receiving antenna location, allows calculation of a line-of-sight from each receiving antenna position to the transmitting antenna. As in conventional DF systems, the intersection of these lines-of-sight provide a position estimate sufficient to initialize phase difference tracking. A third method employs a large number of receiving antennas. When the number of such antennas is sufficiently large, a unique transmitter position can be determined, although the amount of computation increases dramatically with the number of receiving antennas.

The third method of establishing an initial position of the transmitting antenna requires finding its position in a large workspace with no information other than phase difference of received signals. The solution is found as follows: For each pair of receive antennas, the path length difference is an integer number of signal wavelengths plus a fractional part of a wavelength. The phase difference in the two received signals is a measure of the fractional wavelength part of the path length difference. The workspace geometry determines the range of possible integer values of path length difference. Each integer value defines a different hyperbola of revolution. By evaluating all possible combinations of integer values, one combination for each receiver pair, the point where all the hyperbolas intersect is found. This point then represents the initial position of the transmitting antenna.

Each signal enables identification and tracking of single energy source. In one preferred embodiment, a single unmodulated frequency is transmitted. The signal is switched between each of the marker antennas located on a subject of motion study in a known sequence. The signal is emitted from the marker antennas and the propagated signal is received by a plurality of receiving antennas. The receiving apparatus uses the known switching sequence to identify the transmitter associated with each emitted signal and the uses the procedures described above to estimate the position of each marker antenna.

In another embodiment, each marker antenna transmits the same carrier frequency modulated with a different orthogonal signature waveform or code sequence. The receiving apparatus uses the orthogonality of these signature codes to separate the signals from each marker antenna. The receiving apparatus then uses the procedures described above to estimate the position of each marker antenna. Because the orthogonality of the code sequences allows the receiving apparatus to separate the signals from the marker antennas, all marker antennas can transmit all the time. Continuous tracking of each one of the marker antennas is thereby enabled. This technique supports use of spread spectrum transmissions. The two preceding embodiments can be used in combination, each signature code being time-multiplexed between several marker antennas.

An appreciation of other aims and objectives of the present invention may be achieved by studying the following description of preferred and alternate embodiments and by referring to the accompanying drawings.

A BRIEF DESCRIPTION OF THE DRAWINGS

FIG. 1 is schematic diagram of an application of the present invention. It depicts a person who moves in a volume of space and on whom transmitting antennas are placed whose signals are tracked by receiving antennas. The receiving antennas deliver signal phase information to a computer for calculation of the persons body motion.

FIG. 4a is a chart of Body Motion Tracking System accuracy versus processing time showing regions of desired accuracy and processing time for four categories of applications of the present invention.

Figure 5:
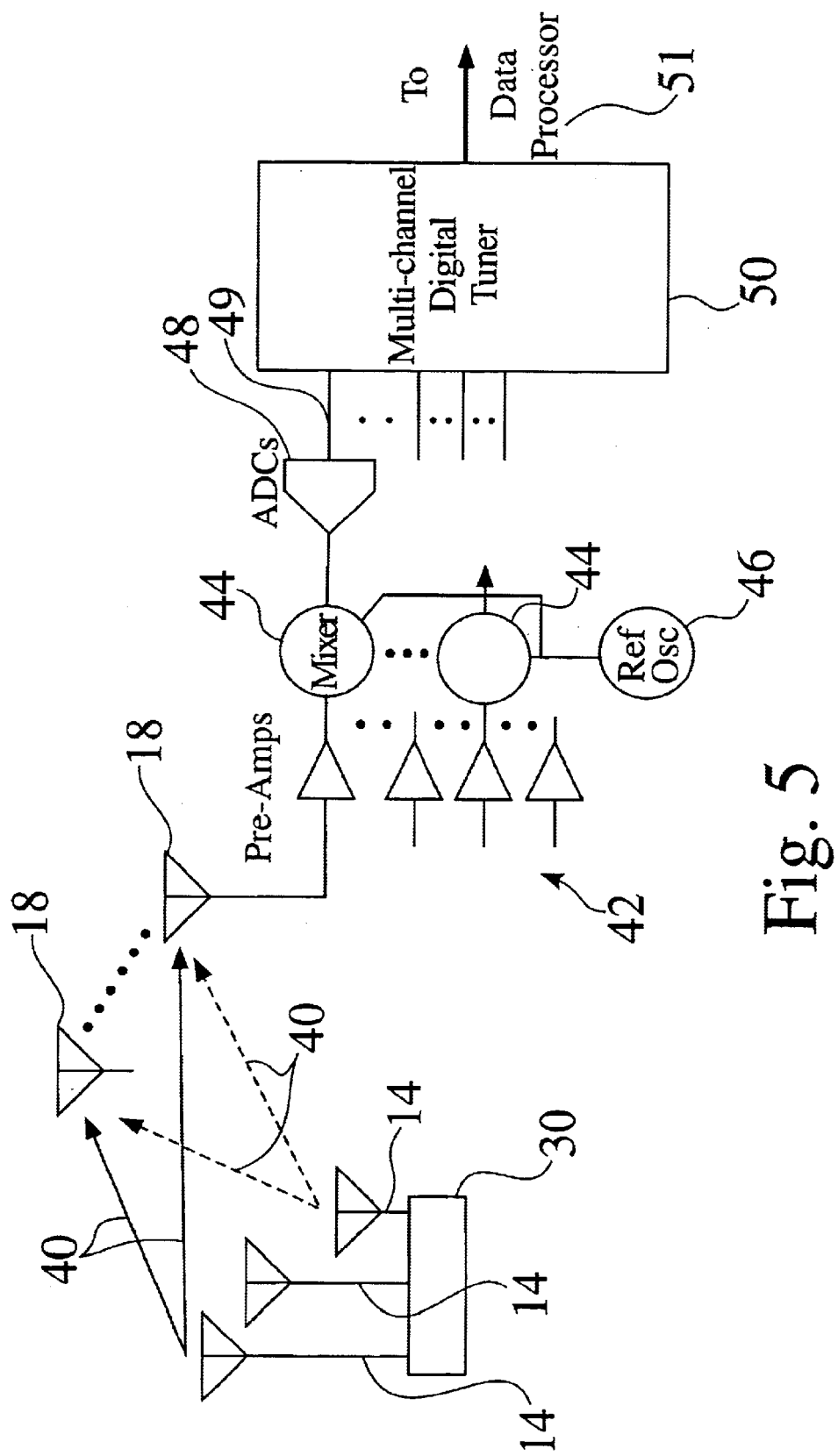

FIG. 5 reveals a block diagram of the radio frequency apparatus used in the present invention to track and measure human body movement.

Figure 6:
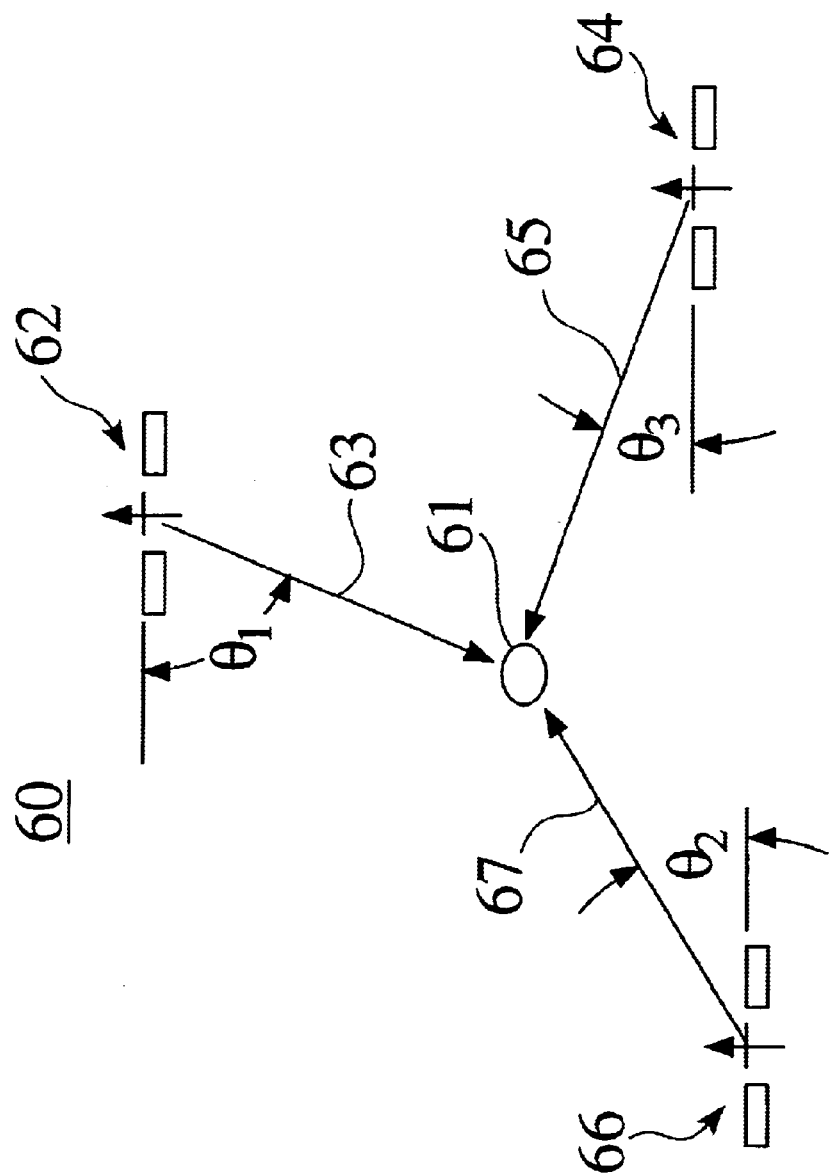

FIG. 6 is a schematic diagram describing the prior art of direction finding by "triangulation" as a method for estimating the position of a source of radio frequency energy.

Figure 6A:
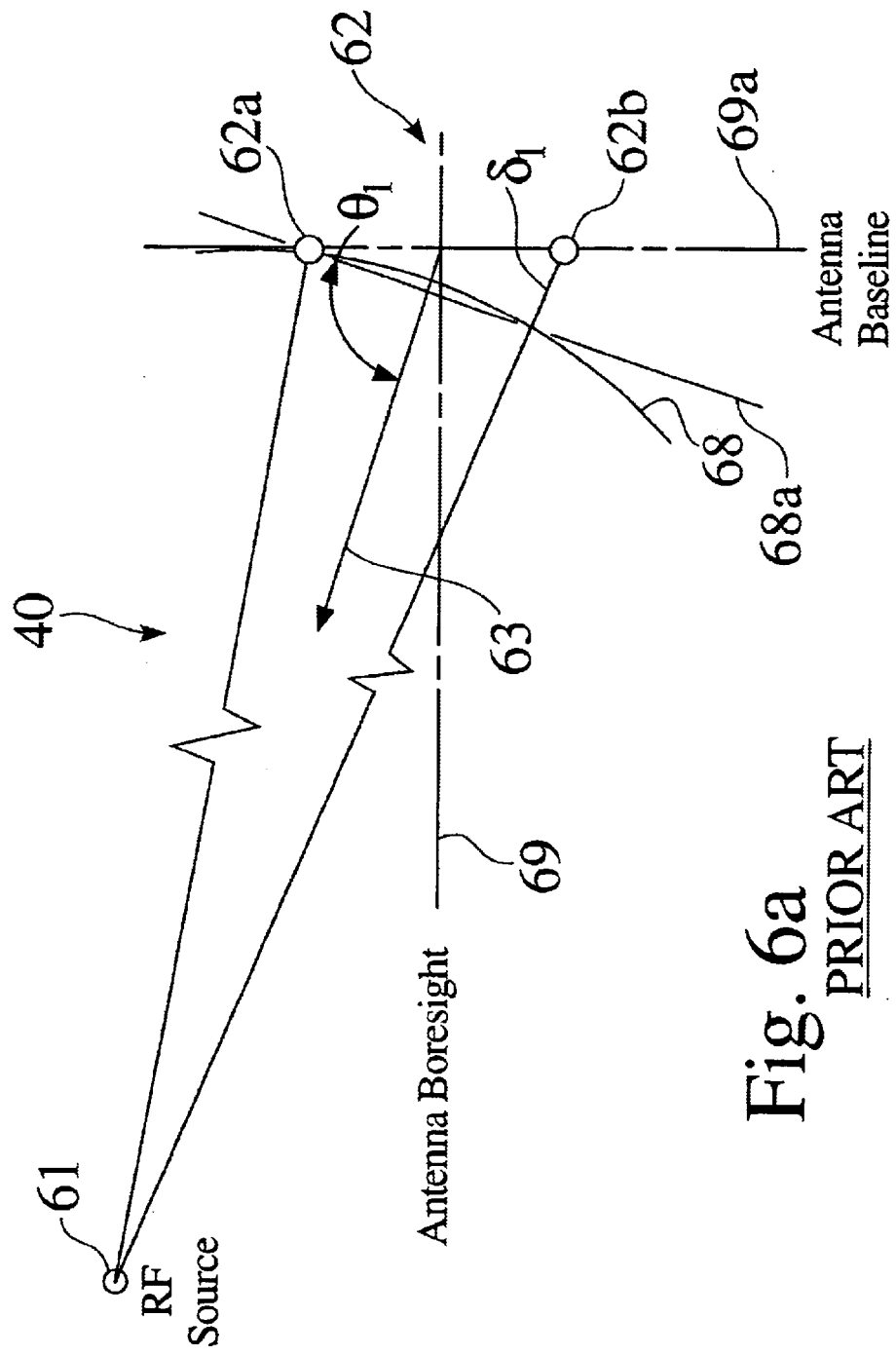

FIG. 6a is a further diagram describing prior art of direction finding which depends on the assumption that an RF source lies at an angle to the receiving antenna boresight line and the received wave front is planar.

Figure 7:
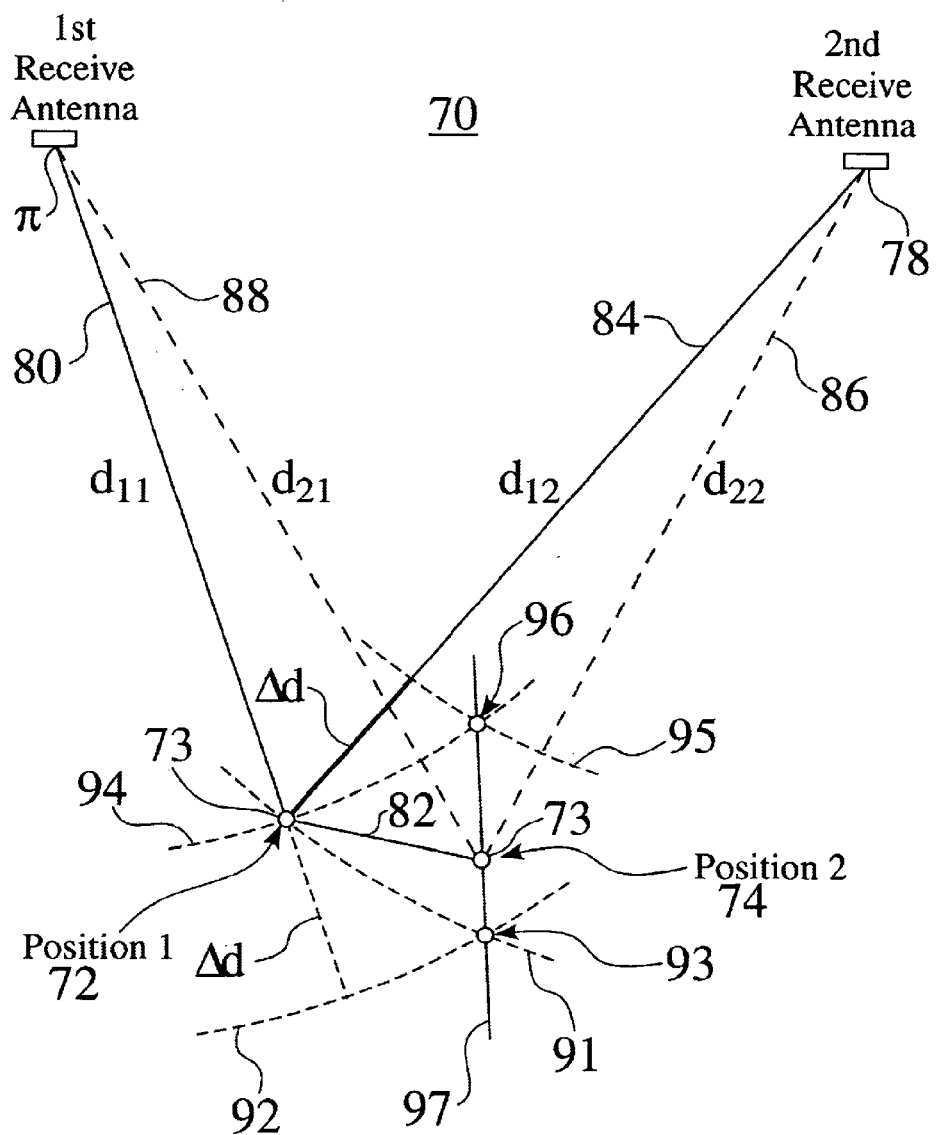

FIG. 7 depicts a schematic diagram of a method used in the present invention to measure by phase differences the relative position and motion of a source of radio frequency energy at widely separated antennas.

Figure 8:
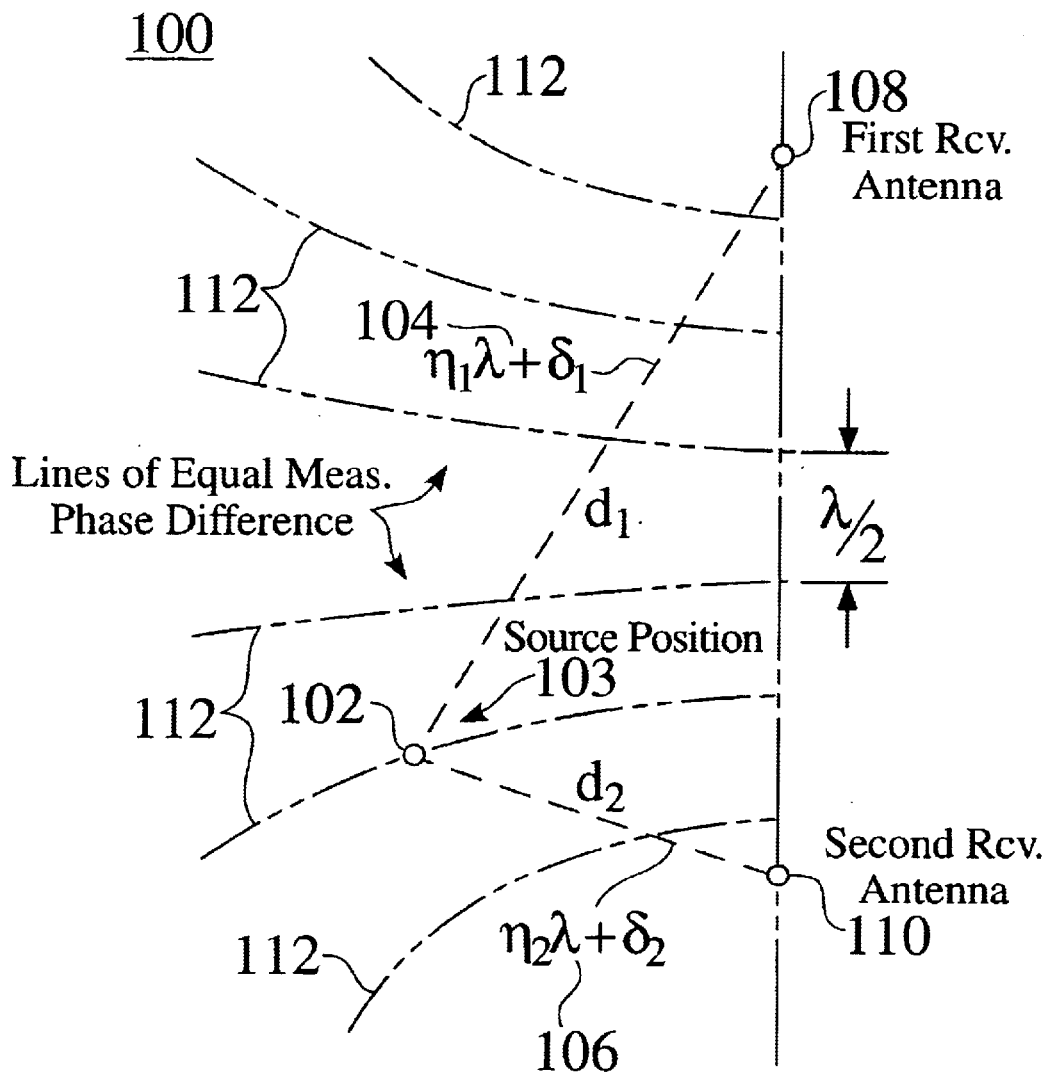

FIG. 8 presents a schematic diagram illustrating a method used in the present invention to estimate the position of an RF energy source using best-fit phase differences at a number of receiving antennas.

A DETAILED DESCRIPTION OF PREFERRED & ALTERNATIVE EMBODIMENTS

Motion Capture

Figure 1:
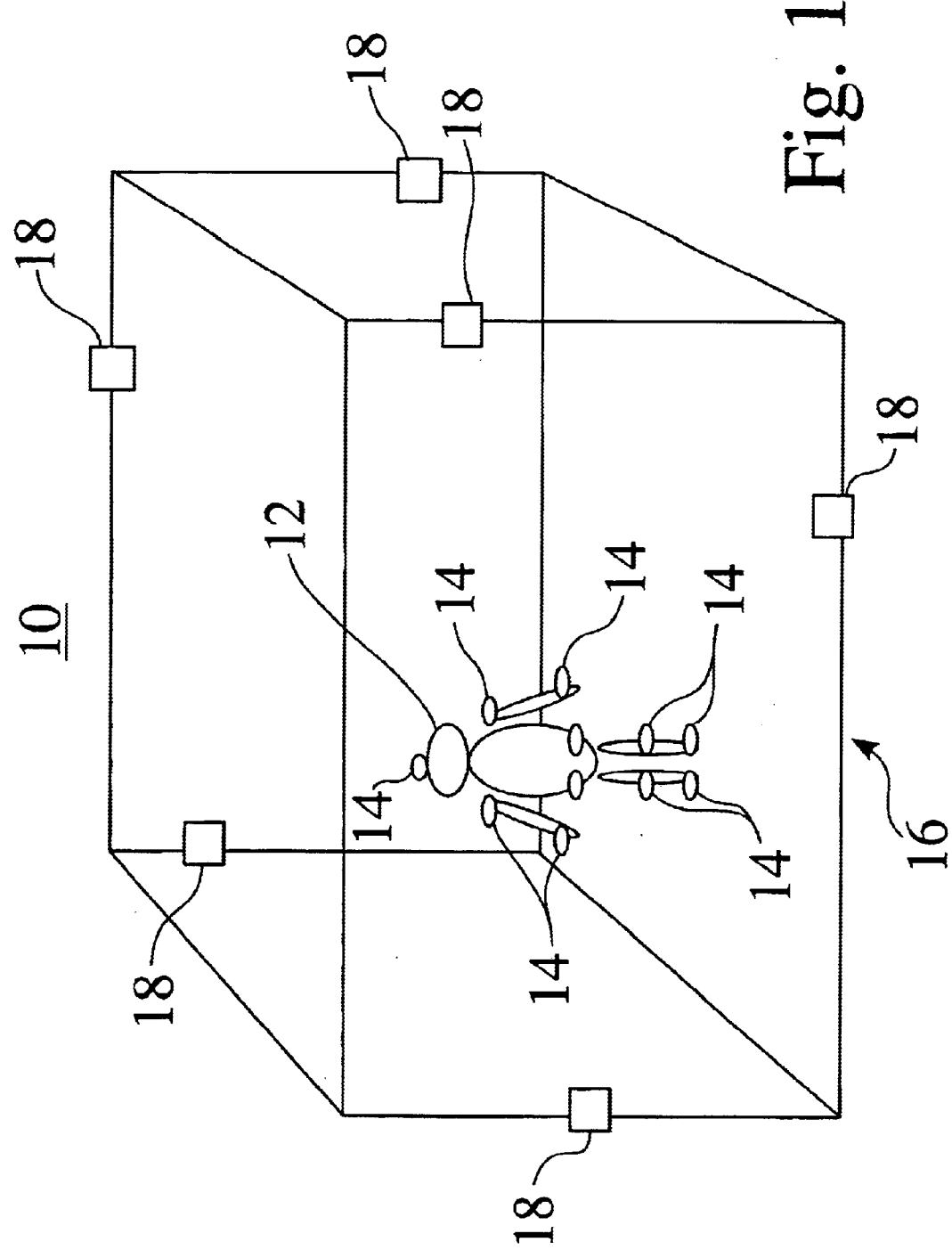

FIG. 1 is a schematic diagram of an application of the present invention which illustrates its features for capturing the position and movement of a subject body. The drawing depicts a subject person 12 who moves in a volume 16 of space and on whom "marker" antennas 14 are placed whose signals are tracked by receiving antennas 18. Each marker antenna 14 is a source of radiant energy. The receiving antennas 18 are dispersed and describe the boundaries of the volume 16. The receiving antennas 18 and their respective receiver apparatus deliver signal phase information to a computer for calculation of the person's body motion.

A low-power transmitting apparatus is disposed on the subject person 12. The transmitting apparatus supplies RF signal energy 40 to the marker antennas 14. In one preferred embodiment, each marker antenna 14 is separately selected and excited by a conventional switching matrix. The receiving system 42–51 can synchronize itself with the switching sequence because the switching sequence is known in advance. Thus, the receiving system 42–51 always knows which marker antenna 14 is transmitting. The output data of the receiving system 42–51 consists of an marker antenna code and its sequence of positions in volume 16.

Figure 2:
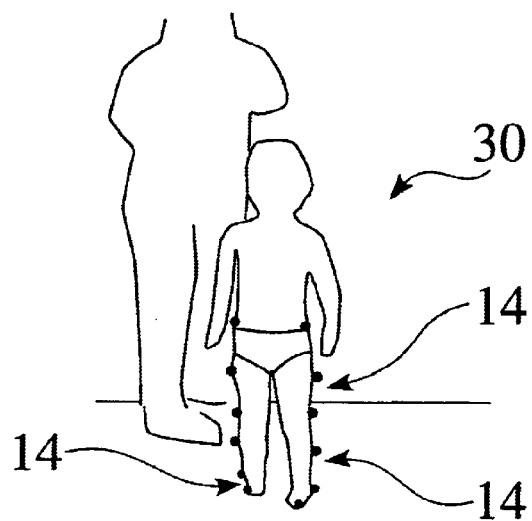
FIG. 2 is a photograph of a child on whom transmitting antennas are disposed.

FIG. 2 is a photograph of a child 30 on whose lower extremities a plurality of marker antennas 14 are disposed. Over twelve million people in the United States have lower extremity disabilities, according to the U.S. Dept. of Health and Human Services (1994). Five hundred thousand Americans have cerebral palsy, growing at the rate of 4,500 cases per year. Extension of these statistics to the entire world population indicates how serious is solving the problem of saving time and money if a substantial percentage of these cases is to be treated. Clinical gait analysis is a diagnostic tool for prescribing treatment for those patients who suffer with neuromuscular, musculoskeletal, or neurological impairments. The primary goal in treating a person who has these problems is to correct their functional deficiencies and thereby improve their quality of life. Functional deficiencies are quantified analytically by having the subject perform simple tasks while patterns of limb movements are systematically measured. Motion-capture data reduces the number of surgeries required to correct some problems.

Figure 4:
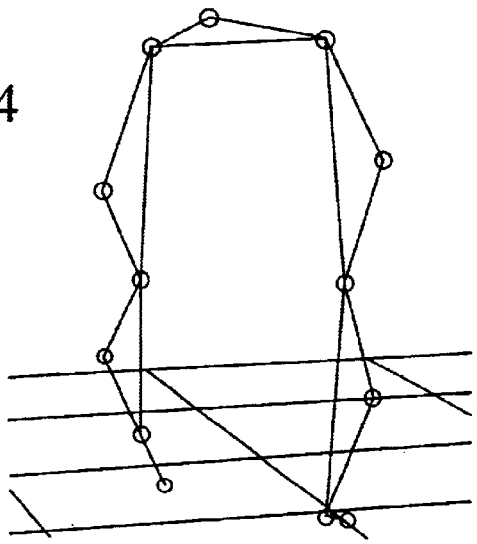
FIG. 4 is a computer presentation of the body position and motion shown in FIG. 3, as seen from a front quarter.
Figure 3:
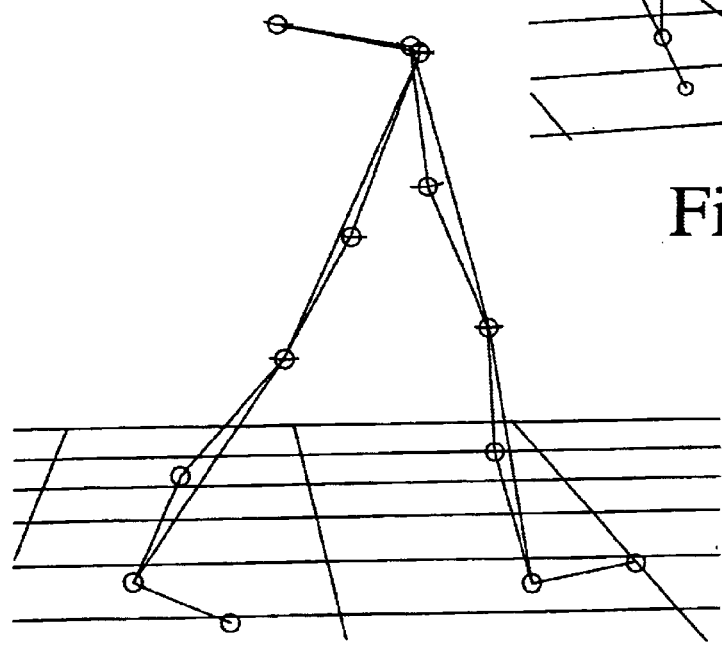
FIG. 3 is a computer presentation of position and motion of the transmitting antennas depicted in FIG. 2, describing the child's body motion as seen from the side.

FIG. 3 is a computer presentation of position and motion of the marker antennas depicted in FIG. 2, describing the child's body motion as seen from the side. FIG. 4 is a computer presentation of the body position and motion as shown in FIG. 3, but seen from a front quarter. It is obvious that the body motion of the child 30 can be viewed on the computer screen in real time both qualitatively and quantitatively. Of course, the data can be save for later referral and comparisons.

Requirements for measurement accuracy, processing time, work-space volume 16 and cost for clinical gait analysis, capabilities of existing devices and capabilities of the present invention are shown in Table 1 below.

TABLE 1

Requirements vs. Capabilities for Body Motion Tracking System

| | Accuracy | Processing Time | Work-Space Volume | Cost |
|---|---|---|---|---|
| Requirements | <1 millimeter | Real Time | Large | Low |
| Existing Devices | 1 to 2 millimeters | Three frames latency | 1 × 2 × 1.5 meters | ≈ $200,000. |
| Body Motion Tracking Capabilities | 1 to 2 millimeters | Real Time | 10 × 10 × 3 meters | ≈ $50,000. |

Besides the direct savings shown above, real-time motion capture reduces the clinical manpower required by about 30%. A large volume in which to work reduces the number of motion-capture data runs, an additional savings of time and manpower.

FIG. 4a is a chart which displays envelopes of requirements for accuracy 20 versus processing time 22 for clinical applications 24 and other applications 23, 25, 26 for the Body Motion Tracking System. Clinical applications 24 are the most demanding for accuracy 20 and processing time 22. Performance improvement applications 23 such as competitive sports and military equipment evaluation, industrial applications 25 and animation 26 in films and television entertainment will clearly benefit from the high accuracy 20 and low processing time 22 of the Body Motion Tracking System.

A block diagram of the Body Motion Tracking System apparatus is revealed in FIG. 5. An RF transmitter 30 drives a plurality of marker antennas 14. Radiated energy signals 40 from the marker antennas 14 are received by a plurality of receiving antennas 18. The radiated signal 40 from a given marker antenna 14 is received by the receiving antennas 18 which are widely separated, at slightly different times because of the different path lengths from the marker antenna 14 to the different receiving antennas 18. The time differential is reflected as a phase difference in the received signal at each receiving antenna 18.

A minimum of four, preferably more, receiving antennas 18 are positioned at the edges of the volume 16 in which the subject body's activity is being conducted. The number of receiving antennas 18 is chosen so that an optimum set can be switched or selected. For each measurement interval, the signals from four to six of the receive antennas are used to estimate marker antenna 14 positions with receive antennas selected by a figure of merit. The figure of merit is ordinarily based on errors, data noise and prediction of clear radiation paths away from the body. Each received signal 40 is boosted in a preamplifier 42 and then down-converted in one of a plurality of mixers 44.

In one preferred embodiment, the RF energy is translated from a microwave frequency of about 2.5 GHz. to an intermediate frequency (IF) of about three Megahertz (MHz). A single reference oscillator 46 is fed to all of the mixers 44 in order to preserve the phase relationships of the RF signals from the receiving antennas 18. Each IF signal is presented to one of a bank of analog-to-digital converters 48 which transform the analog signals 40 to a digital signal format. A common sampling clock, operating in one embodiment at sixteen MHz, is used in this conversion process. Choice of clock frequency depends on the hardware selected and whether direct or sub-sampling is desired. The use of a common clock also preserves the phase relationships of the RF signals 40 received. Digital representations 49 of the received signals are presented to the inputs of a multi-channel digital tuner 50. The digital signals 49 are translated again to about one KHz. Narrow-band filtering and sampling rate reduction are applied. Phase relationships are preserved because all of the signal processing up to this step is "coherent."

The digital data 49 is fed 51 to a main computer and processed to estimate the marker antenna's position relative to each receiving antennal 8. This process is related to conventional direction finding (DF) techniques, but there are significant differences between the present invention and conventional DF. FIGS. 6 and 6a help to understand the conventional DF technique.

Conventional Direction Finding Systems

Conventional DF systems such as shown in FIG. 6, and 6a operate with the assumption that the range 63, 65, 67 from each of the receiving locations 62, 64, 66 to the source antenna 61 is very large relative to the spacing of receiving antenna elements 62a, 62b. Therefore, RF energy wavefront 68 can be represented as a "plane wave" 68a. Each receiving location 62, 64, 66 comprises antenna element pairs 62a, 62b which form simple interferometers. It is also assumed that the RF source 61 is located to one side of the receiving antenna array. In DF techniques, the receiving locations 62, 64, 66 "triangulate" the source 61. In a simple DF system, each receiving location 62, 64, 66 measures the direction to the energy source or "angle of arrival" θ1, θ2, θ3 by phase measurement at pairs of closely spaced antennas 62a, 62b. Position of the source is estimated by finding the intersection of lines drawn from each receiving location 62, 64, 66 along the angle of arrival θ1, θ2, θ3. Because of unavoidable measurement errors, these lines will not all intersect at the same point and the source position 61 is estimated by finding a single point that is closest to all of the lines.

In FIG. 6a, the angle of arrival θ1 is determined by the phase difference between the two receiving antenna elements 62a, 62b. When the source 61 is offset from the antenna boresight line 69, the propagated RF wave front 68a reaches the two antenna elements 62a, 62b at different times. The differential path length δ from the source 61 to the second antenna element 62b and the signal wavelength λ produce the phase difference Δφ at the second antenna element 62b with relation to the first antenna element 62a. If the differential path length δ is less than one wavelength, the phase difference Δφ is given by equation one.

$$\Delta\phi = 2\pi * \delta / \lambda \quad \text{Equation 1.}$$

Simple trigonometry relates the differential path length δ, the distance between the antenna elements and the angle of arrival θ1. This triangulation technique using at least three receivers has substantial inaccuracies in small work volumes and where the signal source 61 lies close to the receiving antennas 62a, b.

Finding Relative Position by Differential Phase Measurement Using Single Antennas The present invention employs differential phase measurement at a plurality of single antennas widely spaced one from the other. FIG. 7 illustrates one preferred embodiment of this technique.

When the energy source 73 is at a starting position 72, the lengths along the paths 80, 84 determine the phase of the propagated signal 60 at a first receive antenna 76 and at a second receive antenna 78. The difference in these phase measurements, $\Delta\phi_1$, is given by Equation 2:

$$\Delta\phi_1 = (2\pi(d_{12} - d_{11})/\lambda) \text{ modulo } 2\pi \quad \text{Equation 2.}$$

where $d_{11}$ is the distance along the path length 80 from the first receive antenna 76 to the energy source 73 at its starting position 72 and $d_{12}$ is the distance from the second receive antenna 78 to the energy source 73 at its starting position 72.

If the energy source 73 moves from its starting position 72 to a second position 74, the new path lengths 88, 86 determine a new phase measurement at the first receive antenna 76 and at the second receive antenna 78. The new phase difference measurement, $\Delta\phi_2$, is given by Equation 3:

$$\Delta\phi_2 = (2\pi(d_{22} - d_{21})/\lambda) \text{ modulo } 2\pi \quad \text{Equation 3.}$$

where $d_{21}$ is the distance along the new path 88 from the first receive antenna 76 to the energy source 73 at its second position 74 and $d_{22}$ is the distance from the second receive antenna 78 to the energy source 73 at its second position 74.

The change in relative phase of the received propagated signal 60 is dependent only on the wavelength λ of the signal 60 and the distance moved 82 by the energy source 73. This system does not require the use of an absolute phase reference.

If the distance moved 82 is small, the change in path length difference is Δd and is given by Equation 4:

$$\Delta d = (d_{22} - d_{21}) - (d_{12} - d_{11}) = \lambda(\Delta\phi_2 - \Delta\phi_1)/2\pi \quad \text{Equation 4.}$$

If one assumes the path 84 from the second receive antenna 78 to the energy source 73 remains a constant length $d_{12}$, then the energy source 73 at its second position 93, would be at the intersection of arc 91 and arc 92. On the other hand, if one assumes the path 80 from the first receive antenna 76 to the energy source 73 remains a constant length $d_{11}$, then the energy source 73 at its second position 96, would be at the intersection of arc 94 and arc 95. If the actual position of the energy source 73 is at the second position 74, then the source 73 will lie on a line 97 drawn through the two points of arc intersection 93 and 96.

Considering the energy source 73 to move in the same plane as that containing the first receive antenna 76 and the second receive antenna 78, a third receive antenna, paired with one of the other two receive antennas 76, 78 would construct a third path to the energy source 73 at its second position 74. The intersection of the first path 88, second path 86 and third path will unambiguously locate the energy source 73.

Consider now a three-dimensional case in which the energy source 73 at its second position 74 does not necessarily lie in the plane defined by the receive antenna locations 76,78 and the energy source 73 at its first position 72. In this case, the second position 74 will lie on a surface, and the line 97 is the intersection of this surface with the plane defined by the receive antenna locations 76,78 and the first position 72. To unambiguously locate the energy source 73 on this surface, two additional receive antennas are required, a total of four receive antennas. Using three different pairs of receive antennas, three such surfaces will be constructed. The position of the energy source 73 will be at the intersection of these three surfaces.

If the absolute starting position 72 of the energy source 73 is known, the new absolute position 74 is then calculated. This procedure is continued for each energy source 73 disposed on a subject body for the duration of the motion-capture process. As already indicated above, the position data is displayed in real time but can be saved for further review and analysis.

Because the change in phase difference $(\Delta\phi_2-\Delta\phi_1)$ can be measured very accurately, the distance moved 82 by the energy source 73 can be measured to small fractions of a wavelength $\lambda$. For a source transmitting at a frequency of 2.45 GHZ, the wavelength $\lambda$ is approximately 12 cm.

Absolute Position Determination Using Phase Differences and Redundancy

An alternative method of finding the absolute position of an energy source within a given volume uses a best-fit phase difference measurement. This method 100 is illustrated in FIG. 8 for two receiving antennas 108, 110 and one energy source 102. The distance d between the transmitter source 102 and a receiver 108, 110 can be represented by an integer number n of wavelengths $\lambda$ plus a fraction $\delta$ of one wavelength as shown in Equation 5.

$$d=n\lambda+\delta \qquad \text{Equation 5.}$$

Because the transmitted signal is sinusoidal, the measured phase difference is equal to the total phase difference modulo $2\pi$. This is mathematically shown in Equation 6. When $|\delta_2-\delta_1|$ is less than one wavelength $\lambda$:

measured phase difference=$(2\pi/\lambda)(d_2-d_1)$ modulo $2\pi$ $=(2\pi/\lambda)(n_2\lambda+\delta_2-n_1\lambda-\delta_1)$ modulo $2\pi$ $$=(2\pi/\lambda)(\delta_2-\delta_1) \qquad \text{Equation 6.}$$

Thus, all integer values of $n_1$ and $n_2$ give the same measured phase difference. Each pair of values of $n_1$ and $n_2$ defines a different hyperbola of revolution 112, the two receiving antennas 108, 110 being the foci. For each pair of receiving antennas 108, 110, the allowable values of $n_2-n_1$ for a source within the measurement volume are:

$$\Delta n=n_2-n_1=0,\pm 1,\pm 2,\ldots \pm N \qquad \text{Equation 7.}$$

Where N is the number of half-wavelengths between the two receiving antennas 108, 110. The source 102 position is found by choosing a value of $\Delta n$ for each pair of receiving antennas 108, 110 such that all of the surfaces of revolution 112 intersect at the same point, that being the source 102 position. For two pairs of receiving antennas 108, 110 (three antennas in all) there are many points of intersection. As more receiving antennas 108, 110 are added to the receiving system, the number of ambiguous solutions is reduced until only one, correct solution remains.

The solution is implemented by evaluating all allowable values of $\Delta n$ for each antenna pair 108, 110 and selecting the set of values of $\Delta n$ for which all the surfaces of revolution 112 intersect at the same point 102. This technique has been validated by simulation.

If the source position is known to be in a suitably small region, then all of the ambiguous solutions are outside of this region even for a minimum number of receiving antennas 108, 110 needed to locate the source 102 in three dimensions. That number is ordinarily four. Only one solution, the true one, is found inside the workspace volume searched. The conditions are satisfied if (1) the approximate source 102 starting position is known; or (2) the source 102 position has been estimated a short time earlier and the current position is limited by the maximum speed the source 102 is able to travel. This technique has been evaluated also in simulation.

In order to extend the work-space volume, additional banks of receiving antennas can be switched into use as the subject moves into their area of coverage. Such bank-switching antennas are useful in studying body motion of racers in a 50-yard dash, for example.

Tracking Multiple Energy Sources

Referring again to FIG. 5, a propagated signal 40 enables identification and tracking of individual energy sources 14. In one preferred embodiment, a single unmodulated frequency is transmitted. The propagated signal 40 is switched between each of the marker antennas 14 located on a subject 12 of motion study in a known sequence, and it is received by a plurality of receiving antennas 18. The receiving apparatus 42–51 uses a known switching sequence to identify the marker antenna 14 associated with each data interval. The collection of data intervals from a single marker antenna are processed as described for the case of a single marker.

In another embodiment, each marker antenna 14 transmits the same carrier frequency modulated with a different orthogonal signature waveform or code sequence. The receiving apparatus 42–51 uses the orthogonality of these signature codes to separate the signals from each marker antenna 14. The receiving apparatus 42–51 then uses the procedures described above to estimate the position of each marker antenna 14. Because the orthogonality of the code sequences allows the receiving apparatus to separate the signals from the marker antennas, all marker antennas can transmit all the time. Continuous tracking of each one of the marker antennas 14 is thereby enabled. This technique supports use of spread spectrum transmissions.

The two preceding embodiments can be used in combination, each signature code being time-multiplexed between several marker antennas 14.

Alternate Embodiments

The discussion to this point has been directed principally to human body motion and in particular to clinical gait analysis in order to understand the concepts and certain embodiments of the present invention. Perhaps an even larger area of application is that of performance improvement. This includes motion studies for athletes and their coaches, evaluations of military personal equipment, combat training and virtual representation of real-life scenarios. Animation in computer games and presentations, industrial uses for measuring human-machine interfaces and machines (such as manufacturing robots) alone can profit from real-time, high-accuracy, low-cost motion studies.

Conclusion

Although the present invention has been described in detail with reference to particular preferred and alternative embodiments, persons possessing ordinary skill in the art to which this invention pertains will appreciate that various modifications and enhancements may be made without departing from the spirit and scope of the claims that follow. The various hardware and software configurations that have been disclosed above are intended to educate the reader about preferred and alternative embodiments, and are not intended to constrain the limits of the invention or the scope of the claims. The List of Reference Characters which follows is intended to provide the reader with a convenient means of identifying elements of the invention in the Specification and Drawings. This list is not intended to delineate or narrow the scope of the claims.

List of Reference Characters

FIG. 1

10 Body motion marker and receiving antennas
12 Subject of motion study
14 Marker antenna
16 Volume of space in which the subject moves
18 Receiving antenna

FIG. 2

14 Marker antenna
30 Child subject of motion study

FIG. 4a

20 Accuracy scale
22 Processing Time scale
23 Performance improvement applications envelope
24 Clinical applications envelope
25 Industrial applications envelope
26 Animation applications envelope

FIG. 5

14 Marker antenna
18 Receiving antenna
30 Low-power RF transmitter
40 Propagated RF signal from marker antenna
42 Receiver pre-amplifier
44 RF Mixer
46 Reference oscillator
48 Analog-to-digital (ADC) converter
49 Digitized IF signal
50 Multi-channel digital tuner
51 Data feed to data processor FIGS. 6 & 6a 40 Propagated signal
60 Prior art system of position-finding triangulation using angle of arrival (AOA) information
61 RF energy source
62 Receiving antenna array 62a Receiving antenna first element
62b Receiving antenna second element
63 Direction to source from first antenna array
64 Second receiving antenna array
65 Direction to source from second antenna array
66 Third receiving antenna array
67 Direction to source from third antenna array
68 RF propagation wavefront
68a Assumed planar wavefront
69 Antenna boresight line
69a Antenna baseline
θ1 Angle of arrival at first receiving antenna array
θ2 Angle of arrival at second receiving antenna array
θ3 Angle of arrival at third receiving antenna array

FIG. 7

70 Sketch of the method of measuring relative position and motion of an energy source
72 Energy source's first position
73 Energy source
74 Energy source's second position
76 First receive antenna
78 Second receive antenna
80 Path from source at first position to first receiving antenna
82 Path on which source moves from first to second position
84 Path from source at first position to second receiving antenna
86 Path from source at second position to second receiving antenna
88 Path from source at second position to first receiving antenna
91 Arc centered on second receive antenna having a radius of $d_{12}$
92 Arc centered on first receive antenna having a radius change determined by total phase change in signal received at first receive antenna
93 Source position assuming distance from source to second antenna remains constant
94 Arc centered on first receive antenna having a radius of $d_{11}$
95 Arc centered on second receive antenna having a radius change determined by total phase change in signal received at second receive antenna
96 Source position assuming distance from source to first antenna remains constant
97 Locus of possible new positions of the energy source measured by phase change at two receiving antennas
Δd Change in path length (range) difference corresponding to measured phase change
$d_{11}$ Length of path from energy source at first position to first receive antenna
$d_{12}$ Length of path from energy source at first position to second receive antenna
$d_{21}$ Length of path from energy source at second position to first receive antenna
$d_{22}$ Length of path from energy source at second position to second receive antenna

FIG. 8

100 Sketch of the method used in the present invention to estimate the position of an RF energy source using best-fit phase differences at a number of receiving antennas.

102 Energy source
103 Position of energy source
104 Distance from the energy source to a first receiving antenna (No. of signal wavelengths plus a fractional signal wavelength)

106 Distance from the energy source to a second receiving antenna (No. of signal wavelengths plus a fractional signal wavelength)
108 First receiving antenna
110 Second receiving antenna
112 Lines of equal measured phase difference
$d_1$ Distance from energy source to first receive antenna
$d_2$ Distance from energy source to second receive antenna
$\lambda$ Transmitter signal wavelength
$n_1$ Integer number of wavelengths from source to first receive antenna
$n_2$ Integer number of wavelengths from source to second receive antenna
$\delta_1$ Fractional wavelengths from source to first receive antenna
$\delta_2$ Fractional wavelengths from source to second receive antenna

What is claimed is:

1. A method for capturing the position and movement of a subject living body comprising the steps of:

providing a transmitter (73); said transmitter (73) disposed on a subject (12) at a location to be tracked; said subject (12) moving from position-to-position within a volume of space (16);

emitting a signal (40) from transmitter (73);

providing a plurality of widely-spaced receiving antennas (76, 78) disposed at edges of said volume of space (16);

measuring a phase difference ($\Delta\phi 1$) of said signal (40) being received at each independent pair of said plurality of receiving antennas (76, 78) when said transmitter (73) is at a first position (72);

changing a physical position of said transmitter (73) from a first position (72) to a second position (74);

measuring a phase difference ($\Delta\phi 2$) of said signal (40) being received at each said independent pair of said plurality of receiving antennas (76, 78) when said transmitter (73) is at a second position (74); and estimating a change in said physical position of said transmitter (73) by comparing measured phase differences ($\Delta\phi 1, \Delta 2$) of received said signal (40) at each said independent pair of said plurality of receiving antennas (76,78).

2. The method as claimed in claim 1, in which the step of providing a transmitter (73) disposed on a subject (12) includes the step of providing a low-power radio frequency transmitter (30) coupled to a marker antenna (14) on said subject (12).

3. The method as claimed in claim 2, in which the step of emitting a signal (40) from said transmitter (73) includes emitting a microwave signal (40) from said marker antenna (14).

4. The method as claimed in claim 3, in which said plurality of receiving antennas (76, 78) includes at least four receiving antennas.

5. The method as claimed in claim 1, in which the step of estimating a change in said physical position (72, 74) of said transmitter (73) by comparing measured phase differences ($\Delta\phi$) of received said signal (40) at each one of said plurality of receiving antennas (76, 78) further includes the steps of:

measuring a signal phase ($\phi$) at each one said widely spaced plurality of receiving antennas (76, 78) when said subject living body (12) is at a first position;

moving said transmitter (73) with said subject living body (12) from said first position (72) a distance (82) to said second position (74);

measuring a change of said received signal phase ($\Delta\phi$) at each of said widely spaced plurality of receiving antennas (76, 78) when said energy source is at said second position (74);

estimating the direction of motion and the distance 82 moved by comparing said measured change of received signal phase ($\Delta\phi$) at said widely-spaced plurality of receiving antennas (76, 78); said received signal phase ($\phi$) being dependent only on a signal wave length ($\lambda$) and said distance and direction moved (82) by said transmitter (73); and continuing said movement (82) and repeating said signal phase measurements, thereby tracking the direction and motion of said transmitter (73) without use of an absolute phase reference.

6. The method as claimed in claim 1, in which the step of estimating a change in said physical position (72, 74) of said transmitter (73) by comparing measured phase differences ($\Delta\phi$) of received said signal (40) at each one of said plurality of receiving antennas (76,78) further includes the steps of:

measuring a signal phase difference ($\Delta\phi$) of received said signal (40) at each one of said widely spaced plurality of receiving antennas (76,78);

evaluating all allowable values of a difference of pairs ($\Delta n$) of integer values (n1, n2) which give the same said measured value of said signal phase difference ($\Delta\phi$);

selecting a set of said values of a difference of pairs ($\Delta n$) of integer values (n1, n2) for which surfaces of all hyperbolas of revolution which are defined by said difference of pairs ($\Delta n$) of integer values (n1, n2) intersect at a same point; and said same point of intersection being said physical position (74) of said transmitter (73) at the time of said signal phase difference ($\Delta\phi$) measurement.

7. The method as claimed in claim 6, in which said microwave signal is at a frequency of approximately 2.4 GHz.

8. The method as claimed in claim 7, adapted to mapping of human muscle, joint and bone interactions for performing clinical gait analysis of persons having neuromuscular, musculoskeletal, or neurological impairments.

9. The method as claimed in claim 7, adapted to mapping and analysis of human body motion for improving performance in sports.

10. The method as claimed in claim 7, adapted to mapping human body motion for evaluation of human interaction with military equipment.

11. The method as claimed in claim 7, adapted to tracking body motion of humans and animals for implementing realistic animation in film and television entertainment.

12. The method as claimed in claim 7, adapted to tracking body motion of humans and animals for implementing realistic animation in computer games and presentations.

13. An apparatus for capturing the position and movement of a subject living body comprising the steps of:

a transmitter (73); said (73) disposed on a subject (12) at a location to be trucked; said subject (12) moving from position-to-position within a volume of space (16); said transmitter source (73) emitting a signal (40);

a plurality of widely-spaced receiving antennas (76, 78), each one of said plurality of receiving antennas (76, 78) being disposed at edges of said volume of space (16);

a phase difference ($\Delta\phi 1$), of said emitted signal (40) being measured at each independent pair of said plurality of receiving antennas (76, 78) when said transmitter energy-source (73) is at a first position (72);

a phase difference ($\Delta\phi 2$), of said emitted signal (40) being measured at said independent pair of said plurality of receiving antennas (76, 78) after moving said transmitter (73) from a first position (72) to a second position (74); end a change (82) in said physical position (72, 74) of said transmitter source (73) being determined by comparing a change in said measured phase difference ($\Delta\phi 2 - \Delta\phi 1$) of received said signal (40) at each said independent pair of said plurality of receiving antennas (76, 78).

14. The apparatus as claimed in claim 13, in which said transmitter (73) disposed on a subject (12) includes a low-power radio frequency transmitter (30) coupled to a marker antenna (14).

15. The apparatus as claimed in claim 14, in which said emitted signal (40) from said transmitter (73) includes a microwave signal (40) from said marker antenna (14).

16. The apparatus as claimed in claim 15, in which said microwave signal is at a frequency of approximately 2.5 GHz.

17. The apparatus as claimed in claim 15, in which said plurality of receiving antennas includes at least four receiving antennas.

18. The apparatus as claimed in claim 13, in which:

the direction of motion and the distance moved (82) by said transmitter (73) being dependent only on a signal wave length ($\lambda$) and a change of relative phase of the received, propagated signal (40); and said measurements being repeated as said movement (82) continues, thereby tracking the direction and motion of said transmitter (73) without use of an absolute phase reference.

19. A method A method for capturing the position and movement of a subject living body comprising the steps of:

providing a transmitter (102); disposing said transmitter (102) on a subject (12) at a location to be tracked; said subject (12) moving from position-to-position within a volume of space (16);

emitting a signal (40) having a wavelength ($\lambda$) from said transmitter (102);

providing a plurality of widely-spaced receiving antennas (108, 110) disposed at edges of said volume of space (16);

representing a length (d) of each signal path (104, 106) from said transmitter (102) to each one of said plurality of widely-spaced receiving antennas (108, 110) as an integer number (n) of said signal wavelengths ($\lambda$) plus a fractional signal wavelength ($\delta$); a difference in signal path length ($\Delta d$) to each one of any pair of said plurality of widely-spaced receiving antennas (108, 110) being characterized by a difference of said integer numbers (n1−n2) multiplied by said signal wavelength ($\lambda$) plus a difference in said fractional signal wavelengths ($\delta 1 - \delta 2$);

assuming a plurality of values of integer number difference ($\Delta n$), a first said integer number difference ($\Delta n1$) being characterized as a first integer value (n1) less a second integer value (n2), a second said integer number difference ($\Delta n2$) being characterized as a third integer value (n3) less a fourth integer value (n4) and so on, for each value of integer number difference ($\Delta n$) possible within said volume of space (16);

measuring a phase difference ($\Delta\phi$) between each said signal (40) received from said transmitter (102) at each said pair of said plurality of receiving antennas (108, 110); each one of said plurality of values of integer number difference ($\Delta n$) and each said measured phase difference ($\Delta\phi$) defining a surface of locations (112) upon which said transmitter (102) may be located;

selecting one of said plurality of values of integer difference ($\Delta n$) for each pair of said plurality of receiving antennas (108, 110) and calculating a potential location (103) having a smallest mean square distance from all of the surfaces of location (112) defined by said selected values of integer difference ($\Delta n$) and said measured phase differences ($\Delta\phi$);

iterating said calculations of said potential energy source location using all of said assumed plurality of values of integer difference ($\Delta n$) possible within said volume of space (16) and finding each said position (103) until a final absolute energy-source position (103) is found at which a smallest said mean square distance from corresponding said surfaces of location (112) exists.

20. The method as claimed in claim 19, in which the step of providing a plurality of widely-spaced receiving antennas (108, 110) disposed at edges of said volume of space (16), includes providing at least four widely-spaced receiving antennas.

21. The apparatus as claimed in claim 19, in which said transmitting means (73) includes a low-power, radio frequency transmitter (30) coupled to a marker antenna (14).

22. The apparatus as claimed in claim 21, which said emitted signal (40) from said transmitter (73) includes a microwave signal (40) emitted from said marker antenna (14).

23. The apparatus as claimed in claim 22, in which said microwave signal is at a frequency of approximately 2.5 GHz.

24. The apparatus as claimed in claim 22, adapted to mapping of human muscle, joint and bone interactions for performing clinical gait analysis of persons having neuromuscular, musculoskeletal, or neurological impairments.

25. The apparatus as claimed in claim 22, adapted to mapping and analysis of human body motion for improving performance in sports.

26. The apparatus as claimed in claim 22, adapted to mapping human body motion for evaluation of human interaction with military equipment.

27. The apparatus as claimed in claim 22, adapted to tracking body motion of humans and animals for implementing realistic animation in film and television entertainment.

* * * * *